(12) United States Patent
Kim et al.

(10) Patent No.: US 12,029,595 B2
(45) Date of Patent: Jul. 9, 2024

(54) METHOD FOR MANUFACTURING CRISS-CROSS TYPE X-RAY GRID

(71) Applicant: JPI HEALTHCARE CO., LTD., Seoul (KR)

(72) Inventors: Jin Guk Kim, Seoul (KR); Jin Won Kim, Seoul (KR); Won Sik Yoon, Suwon-si (KR); Myung Kyu Park, Siheung-si (KR); Ho Kwon Cha, Ansan-si (KR)

(73) Assignee: JPI HEALTHCARE CO., LTD., Seoul (KR)

( * ) Notice: Subject to any disclaimer, the term of this patent is extended or adjusted under 35 U.S.C. 154(b) by 498 days.

(21) Appl. No.: 17/309,584

(22) PCT Filed: Oct. 22, 2019

(86) PCT No.: PCT/KR2019/013896
§ 371 (c)(1),
(2) Date: Jun. 7, 2021

(87) PCT Pub. No.: WO2020/138673
PCT Pub. Date: Jul. 2, 2020

(65) Prior Publication Data
US 2022/0015725 A1 Jan. 20, 2022

(30) Foreign Application Priority Data

Dec. 26, 2018 (KR) .................. 10-2018-0169545

(51) Int. Cl.
*A61B 6/42* (2024.01)
*A61B 6/40* (2024.01)
(Continued)

(52) U.S. Cl.
CPC .......... *A61B 6/4291* (2013.01); *A61B 6/4035* (2013.01); *G02B 5/1857* (2013.01); *G02B 5/1866* (2013.01); *G21K 1/025* (2013.01)

(58) Field of Classification Search
CPC .. A61B 6/4291; A61B 6/4035; G02B 5/1866; G02B 5/1857; G02B 2207/123; G21K 1/025
See application file for complete search history.

(56) References Cited

U.S. PATENT DOCUMENTS 5,198,680 A * 3/1993 Kurakake ............... G21K 1/025
250/363.1
5,557,650 A * 9/1996 Guida .................... G21K 1/025
378/154
(Continued)

FOREIGN PATENT DOCUMENTS

KR 10-1131151 B1 3/2012
KR 10-1267615 B1 5/2013
(Continued)

OTHER PUBLICATIONS

International Search Report mailed Jan. 30, 2020, issued in PCT/KR2019/013896, filed Oct. 22, 2019, 5 pages.
(Continued)

*Primary Examiner* — Dani Fox
*Assistant Examiner* — Soorena Kefayati
(74) *Attorney, Agent, or Firm* — Christensen O'Connor Johnson Kindness PLLC

(57) ABSTRACT

A method for manufacturing a criss-cross type X-ray grid may include: forming a plurality of criss-cross type grooves at predetermined intervals in a longitudinal direction and a lateral direction in a substrate made of an X-ray transparent material, through a semiconductor sawing machine, such that the grooves form a checker board shape as a whole; putting the substrate having the criss-cross type grooves
(Continued)

formed therein into a storage tank filled with a molten X-ray absorbent material; filing the criss-cross type grooves, formed in the substrate, with the X-ray absorbent material by vacuuming the inside of the storage tank; and taking the substrate filled with the X-ray absorbent material out of the storage tank, and curing the substrate at room temperature.

12 Claims, 4 Drawing Sheets

(51) Int. Cl.
*G02B 5/18* (2006.01)
*G21K 1/02* (2006.01)

(56) References Cited

U.S. PATENT DOCUMENTS

| | | | | |
|---|---|---|---|---|
| 5,581,592 A * | 12/1996 | Zarnoch | ............... | G21K 1/025 378/154 |
| 6,980,629 B1 * | 12/2005 | Hoheisel | ............... | B33Y 10/00 378/154 |
| 8,265,228 B2 * | 9/2012 | Shaw | ............... | G21K 1/025 378/154 |
| 2003/0072415 A1 * | 4/2003 | Eidam | ............... | B33Y 80/00 378/154 |
| 2005/0046946 A1 * | 3/2005 | Mori | ............... | G02B 5/1852 359/569 |
| 2005/0117707 A1 * | 6/2005 | Baier | ............... | G21K 1/04 378/156 |
| 2008/0317213 A1 * | 12/2008 | Hempel | ............... | G21K 1/10 378/154 |
| 2009/0128893 A1 * | 5/2009 | McCarthy | ............... | G02B 5/3058 977/932 |
| 2010/0020401 A1 * | 1/2010 | Fujimoto | ............... | G02B 5/1857 359/589 |
| 2010/0276829 A1 * | 11/2010 | Yang | ............... | B29C 39/003 264/114 |
| 2011/0069816 A1 * | 3/2011 | Shaw | ............... | A61B 6/4291 378/154 |
| 2011/0122999 A1 * | 5/2011 | Vogtmeier | ............... | B22F 7/002 378/154 |
| 2011/0129070 A1 * | 6/2011 | Klausz | ............... | G21K 1/025 427/160 |
| 2011/0317819 A1 * | 12/2011 | Shaw | ............... | G21K 1/025 427/160 |
| 2012/0307976 A1 * | 12/2012 | Kaneko | ............... | G21K 1/025 378/62 |
| 2015/0325322 A1 * | 11/2015 | Schaepkens | ............... | G21K 1/025 378/154 |
| 2016/0124126 A1 * | 5/2016 | Vasylyev | ............... | G02B 5/003 359/893 |
| 2017/0040076 A1 * | 2/2017 | Yokoyama | ............... | B81C 1/00571 |
| 2018/0268952 A1 * | 9/2018 | Glatz | ............... | G21K 1/025 |

FOREIGN PATENT DOCUMENTS

| | | |
|---|---|---|
| KR | 10-1444731 B1 | 9/2014 |
| KR | 10-2016-0024650 A | 3/2016 |
| KR | 10-1997862 B1 | 7/2019 |

OTHER PUBLICATIONS

Written Opinion mailed Jan. 30, 2020, issued in PCT/KR2019/013896, filed Oct. 22, 2019, with partial machine translation of p. 3, 4 pages.

* cited by examiner

Primary Processing(1D)  Secondary Processing(Crisscross(2D))

METHOD FOR MANUFACTURING CRISS-CROSS TYPE X-RAY GRID

TECHNICAL FIELD

The present disclosure relates to a method for manufacturing a criss-cross type X-ray grid, and more particularly, to a method for manufacturing a criss-cross type X-ray grid, which includes forming criss-cross type grooves in a checker board shape as a whole by forming a plurality of grooves in a substrate made of an X-ray transparent material in horizontal and vertical directions using a sawing machine, putting the substrate having the criss-cross type grooves formed therein into a storage tank filled with a liquid X-ray absorbent material, and vacuuming the inside of the storage tank such that the liquid X-ray absorbent material tightly fills the criss-cross type grooves formed in the substrate made of an X-ray transparent material, thereby further simplifying the X-ray grid manufacturing process, and simultaneously manufacturing a criss-cross type ultra-density X-ray grid which is difficult to implement through an existing stacking method.

BACKGROUND ART

Recently, with the development of digital industry, most pieces of medical image equipment have been changed and improved in a digital manner According to such a trend, a DR (Digital Radiography) which acquires a digital X-ray image using an existing X-ray tube and a digital radiography image detector has been recently developed to replace an existing X-ray film. Furthermore, in order to improve the diagnosis ability, an X-ray image with a higher quality is required.

The digital X-ray image detector includes a plurality of pixel-type small light detectors which are arranged in a matrix shape, and configured to directly or indirectly detect X-ray energy absorbed at the respective positions thereof, digitalize the absorbed X-ray energy and the position information, and transmit the digitalized energy and information to a microprocessor to store or visualize the digitalized energy and information.

When an X-ray image is taken through such an X-ray imaging device, radiation is inevitably scattered in the body of a patient. A part of the scattered radiation reaches a light detector and overlaps primary radiation. That is, the scattered X-ray, which is generated while the X-ray passes through an object, may be detected by another light detector adjacent to a light detector located at a predetermined position, and serve as noise to reduce the contrast of the X-ray image.

In order to solve the above-described problem, Korean Patent No. 1485836 has disclosed a method of fabricating X-ray grids using a pressurizer system. According to the method, a grid made of an X-ray transparent material and an X-ray absorbent material is installed on a front surface of a light detector, and serves to absorb scattered X-ray, which is generated while X-ray passes through an object, thereby preventing the scattered X-ray from acting as noise.

As illustrated in FIG. 1, the conventional X-ray grid disclosed in Korean Patent No. 1485836 has a one-dimensional structure in which strip-shaped X-ray transparent materials 10 and X-ray absorbent materials 20 are alternately arranged in line in parallel to each other, and is configured to absorb scattered X-ray which is generated while X-ray passes through an object.

Furthermore, according to the conventional X-ray grid fabrication method, the X-ray transparent materials and the X-ray absorbent materials are adhered to each other and hardened, followed by a shearing process to form thin and long strips. Then, the strips are individually stacked to have a radial inclination through a jig, and adhered through an adhesive or the like. Thus, the strips are configured to face an X-ray focal point, thereby preventing valid X-ray, which is required to acquire an X-ray image, from being absorbed by the X-ray absorbent materials.

However, the conventional X-ray grid configured in one dimensional manner may relatively effectively block X-rays from scattering in a direction crossing the grid, but have difficulties in blocking X-rays from scattering in a direction parallel to a grid line. In order to solve such a problem, a checker board-shaped criss-cross type grid may be employed to effectively block X-rays from scattering to the right and left and top and bottom. However, when the conventional X-grid fabrication method is used, a criss-cross type grid cannot be formed in one substrate. Thus, two one-dimensional grid substrates are stacked in a criss-cross shape in order to fabricate the criss-cross type grid. As a result, the fabrication process becomes complicated, and the thickness of the fabricated substrate is increased to reduce primary radiation transmission. Therefore, criss-cross type grids are not actively applied in the field.

DISCLOSURE

Technical Problem

Various embodiments are directed to a method for manufacturing a criss-cross type X-ray grid, which includes forming criss-cross type grooves in a checker board shape as a whole by forming a plurality of grooves in a substrate made of an X-ray transparent material in horizontal and vertical directions using a sawing machine, putting the substrate having the criss-cross type grooves formed therein into a storage tank filled with a liquid X-ray absorbent material, and vacuuming, i.e., applying a vacuum to, the inside of the storage tank such that the liquid X-ray absorbent material tightly fills the criss-cross type grooves formed in the substrate made of an X-ray transparent material, thereby further simplifying the X-ray grid manufacturing process, and simultaneously manufacturing a criss-cross type ultra-density X-ray grid which is difficult to implement through an existing stacking method.

Technical Solution

In an embodiment, a method for manufacturing a criss-cross type X-ray grid may include: forming a plurality of criss-cross type grooves at predetermined intervals in a longitudinal direction and a lateral direction in a substrate made of an X-ray transparent material, through a semiconductor sawing machine, such that the grooves form a checker board shape as a whole; putting the substrate having the criss-cross type grooves formed therein into a storage tank filled with a molten X-ray absorbent material; filing the criss-cross type grooves, formed in the substrate, with the X-ray absorbent material by vacuuming the inside of the storage tank; and taking the substrate filled with the X-ray absorbent material out of the storage tank, and curing the substrate at room temperature.

Advantageous Effects

In accordance with the embodiment of the present disclosure, the method for manufacturing a criss-cross type X-ray grid may include forming criss-cross type grooves with a checker board shape as a whole in a substrate made of an X-ray transparent material using a sawing machine, putting the substrate having the criss-cross type grooves formed therein into a storage tank filled with a liquid X-ray absorbent material, and vacuuming the inside of the storage tank such that the liquid X-ray absorbent material tightly fills the criss-cross type grooves formed in the substrate made of an X-ray transparent material, thereby further simplifying the X-ray grid manufacturing process, and simultaneously manufacturing a criss-cross type ultra-density X-ray grid which is difficult to implement through an existing stacking method.

Furthermore, the X-ray grid has the structure in which the X-ray absorbent material is formed to have a cross-cross type structure having a checker board shape as a whole, and thus can effectively block the scattering of the radiation in all directions (i.e. the top, bottom, left and right), which makes it impossible to effectively the quality of an X-ray image.

MODE FOR INVENTION

The present disclosure may be modified in various manners and have various embodiments. Thus, specific embodiments will be illustrated in the accompanying drawings, and described in detail with the reference to the drawings.

However, it should be understood that the present disclosure is not limited to the specific embodiments, but includes all modifications, equivalents and substitutions without departing from the spirit and technical scope of the present disclosure. The terms such as first and second may be used to describe various components, but the components are not limited by the terms. The terms are only used to distinguish one component from another component. For example, a first component may be referred as a second component, and the second component may also be referred to as the first component, without departing from the scope of the present disclosure.

The terms used in this application are used only to describe a specific embodiment, and do not intend to limit the present disclosure. The expression in a singular form may include the expression in a plural form unless referred to the contrary. In this application, it should be understood that the term of "include" or "have" specifies the existence of a property, a number, a step, an operation, an element, a component, or combinations thereof, but does not exclude the possibility of existence or addition of one or more other properties, numbers, steps, operations, elements, components, or combinations thereof.

Hereafter, preferred embodiments of the present disclosure will be described in detail with reference to the accompanying drawings.

First, a method of manufacturing a criss-cross type X-ray grid in accordance with an embodiment of the present disclosure will be described in detail with reference to FIGS. 3 to 5, based on the flowchart of FIG. 2.

Figure 1:
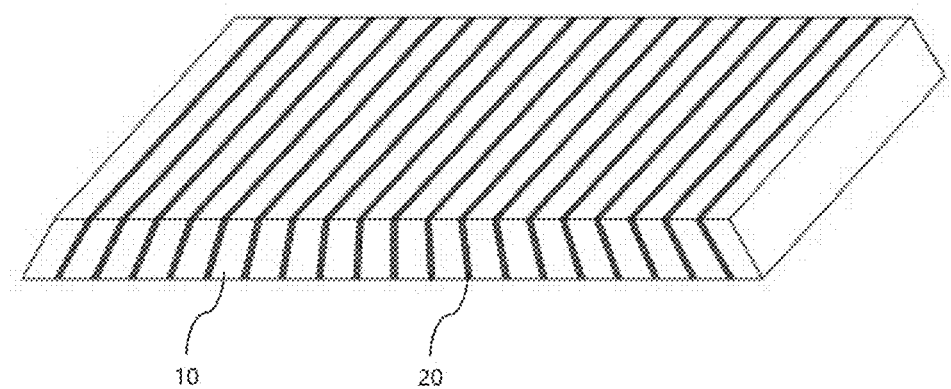
FIG. 1 is a diagram illustrating a conventional one-dimensional X-ray grid.
Figure 2:
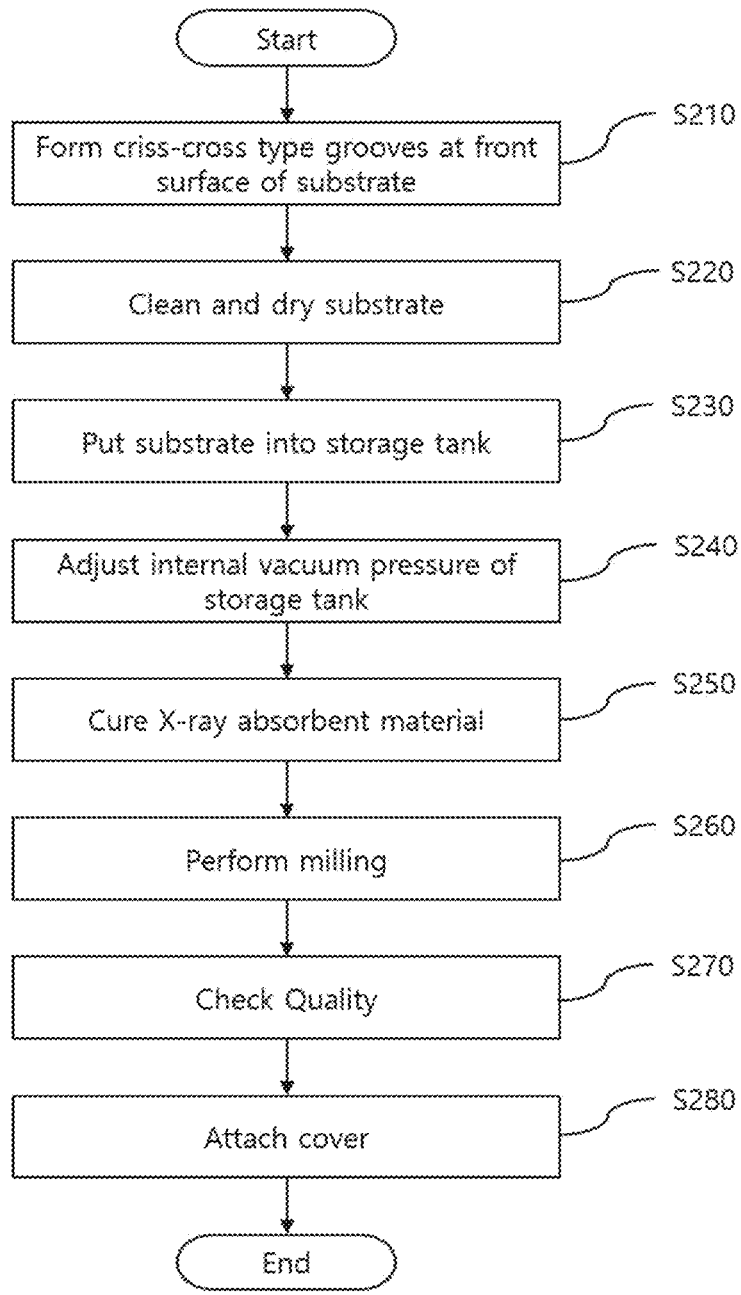
FIG. 2 is a flowchart illustrating a method of manufacturing a criss-cross type X-ray grid in accordance with an embodiment of the present disclosure.

As illustrated in FIG. 2, the method of manufacturing a criss-cross type X-ray grid in accordance with the embodiment of the present disclosure starts with step S210 of forming a plurality of grooves at predetermined intervals in longitudinal and lateral directions at a front surface of a substrate made of an X-ray transparent material.

The criss-cross type grooves formed in the substrate are formed through a semiconductor sawing machine. Such a sawing machine refers to a device that cuts a wafer into separate chips in horizontal and vertical directions during a semiconductor manufacturing process, and may be configured in various manners. For example, the sawing machine may be configured as a mechanical sawing machine such as a wheel blade, wire saw or cutter blade made of diamond, or a thermal sawing machine such as laser. In the present disclosure, it is obvious that any semiconductor sawing machines may be applied as long as the semiconductor sawing machines can form grooves in horizontal and vertical directions at the front surface of a substrate.

Figure 3:
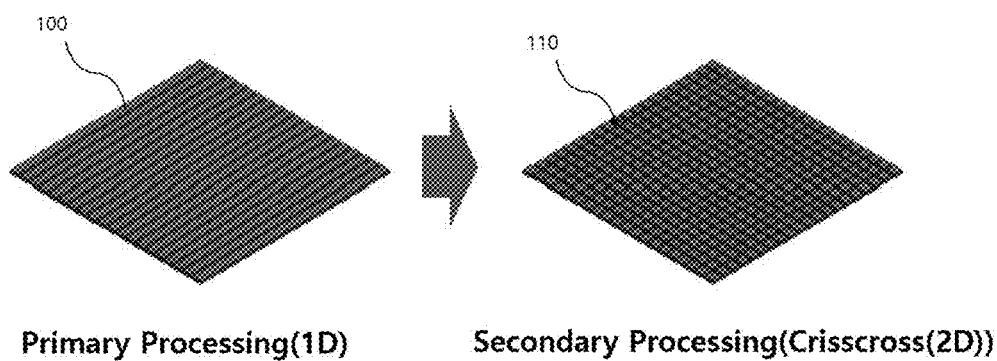
FIG. 3 is a diagram illustrating a substrate in which criss-cross type grooves forming a checker board shape as a whole are formed, in the method of manufacturing a criss-cross type X-ray grid in accordance with the embodiment of the present disclosure.
Figure 4:
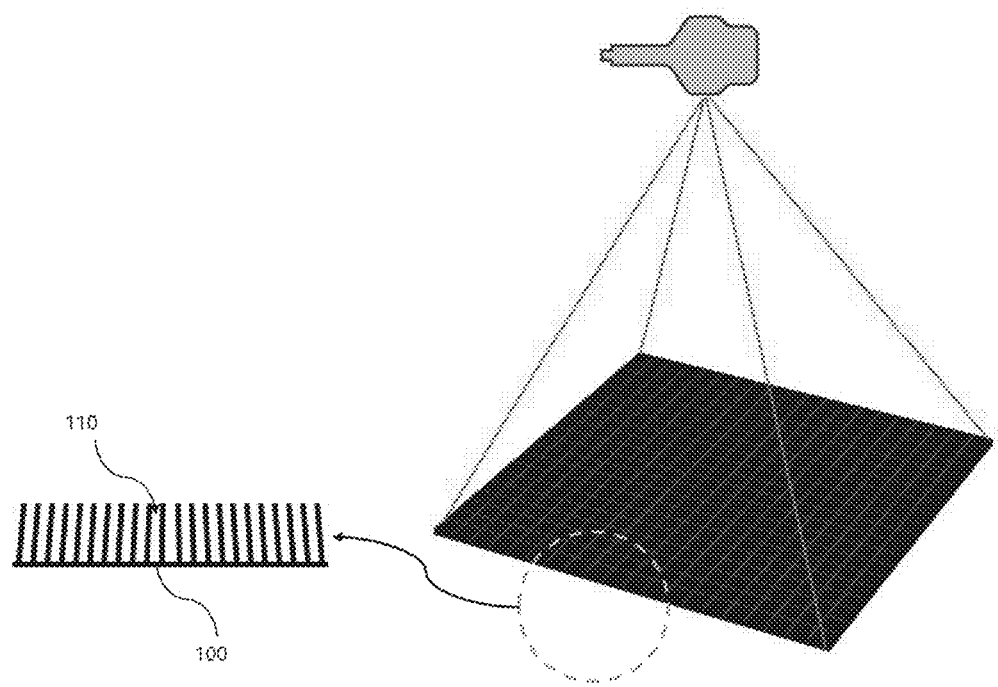
FIG. 4 is a diagram illustrating a substrate having a radial inclination in the method of fabricating a criss-cross type X-ray grid in accordance with the embodiment of the present disclosure.

The criss-cross type grooves in accordance with the embodiment of the present disclosure are formed as illustrated in FIGS. 3 and 4. Specifically, the semiconductor sawing machine is used to form a plurality of grooves at predetermined intervals in a shape to cross the front surface of a substrate 100 in the lateral direction, and then to form a plurality of grooves at predetermined intervals in a shape to cross the front surface of the substrate 100 in the longitudinal direction. Thus, the lateral grooves and the longitudinal grooves, which are formed at the front surface of the substrate, cross each other at 90 degrees, thereby forming criss-cross type grooves 110 to form a checker board shape as a whole. At this time, the criss-cross type grooves 110 may be typically formed to a depth corresponding to 50% to 80% of the thickness of the substrate at the front surface of the substrate, and the number of the formed criss-cross type grooves and the distance between the criss-cross type grooves may be decided as proper values according to the specification of an X-ray detector.

Furthermore, as illustrated in FIG. 4, the criss-cross type grooves 110 are formed to have a predetermined angle and thus inclined toward the center from the center to the left and right ends of the substrate 100. Therefore, the criss-cross type grooves 110 may form a tapered trapezoidal shape as a whole. This is in order to prevent such a problem that the uniformity of an image is degraded as a part of valid X-ray, required for acquiring an X-ray image, as well as scattered X-ray is unnecessarily absorbed by the X-ray absorbent material in the grid and causes the Moire effect to form a wave-shaped image, because an X-ray beam emitted from an X-ray source is emitted in a cone shape.

The substrate 100 in accordance with the present disclosure may be made of plastic, polymer, aluminum, ceramic, graphite or carbon fiber, which has a high X-ray transmission factor. In the embodiment of the present disclosure, graphite is used.

Then, when the criss-cross type grooves 110 are completely formed at the front surface of the substrate 100, foreign matters which occur when the criss-cross type grooves are formed in the substrate are removed from the substrate through a cleaning and drying process using ultrasonic waves, in step S220. During this process, a measurement camera such as a CCD camera may be used to determine whether foreign matters remain and to check the radial inclination angle of the criss-cross type grooves formed at the front surface of the substrate made of an X-ray transparent material.

Figure 5:
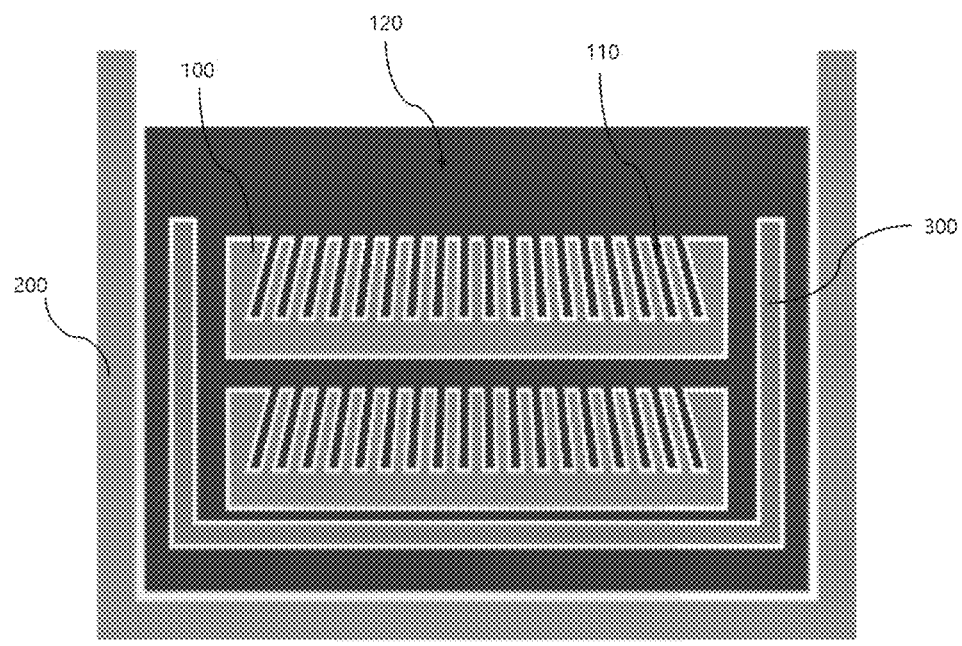
FIG. 5 is a diagram illustrating a process of filling the criss-cross type grooves of the substrate with an X-ray absorbent material, by using a storage tank, in the method of manufacturing a criss-cross type X-ray grid in accordance with the embodiment of the present disclosure.

FIG. 5 is a diagram illustrating a process of filling the criss-cross type grooves formed in the substrate with an X-ray absorbent material by using a storage tank, in accordance with the embodiment of the present disclosure.

As illustrated in FIG. 5, during the process of filling the criss-cross type grooves 110 formed in the substrate 100 with an X-ray absorbent material by using a storage tank 200, the substrate 100 having the criss-cross type grooves 110 formed therein is fixed to a jig 300 and put into the storage tank 200 filled with a liquid X-ray absorbent material 120, in step S230.

At this time, the liquid X-ray absorbent material 120 stored in the storage tank is obtained by melting X-ray absorbent metal. The liquid X-ray absorbent material 120 is heated and molten by a heater (not illustrated) installed in the storage tank 200, and stored as liquid in the storage tank.

As the liquid X-ray absorbent material 120 stored in the storage tank, metallic materials having a lower melting point than the X-ray transparent material forming the substrate 100 may be applied. Examples of the liquid X-ray absorbent material may include lead (Pb), bismuth (Bi) and an alloy of Pb and Bi.

The alloy of Pb and Bi may have the melting point in the range of approximately 200° C. to 400° C. according to a mixing ratio. At this time, according to the types of X-ray transparent materials forming the substrate, the mixing ratio of the alloy forming the X-ray absorbent material is adjusted so that the X-ray absorbent material has a lower melting point than the X-ray transparent material.

Through the heater installed in the storage tank, the internal temperature of the storage tank is maintained at a temperature equal to or higher than the melting point of the X-ray absorbent material, and maintained at a lower temperature than the melting point of the X-ray transparent material forming the substrate, such that the substrate is not molten even though the substrate made of the X-ray transparent material is dipped in the storage tank filled with the X-ray absorbent material molten in a liquid state.

As such, when the substrate 100 made of the X-ray transparent material is put into the storage tank 200 filled with the X-ray absorbent material 120 molten in a liquid state, the criss-cross type grooves 110 formed in the substrate are filled with the liquid X-ray absorbent material 120. Since the criss-cross type grooves 110 formed in the substrate are formed as ultra-fine grooves, it is difficult to tightly fill the criss-cross type grooves 110 with the X-ray absorbent material 120 only through a process of simply dipping the substrate 100 in the storage tank.

Thus, the method in accordance with the present disclosure includes a process of vacuuming the inside of the storage tank filled with the liquid X-ray absorbent material in step S240. That is, the process of vacuuming the inside of the storage tank induces the liquid X-ray absorbent material, stored in the storage tank, to tightly fill the criss-cross type grooves formed in the substrate made of the X-ray transparent material.

At this time, when the vacuum pressure inside the storage tank is excessively low, a filling defect may occur while the criss-cross type grooves are not tightly filled with the X-ray absorbent material. On the other hand, when the vacuum pressure is excessively high, the X-ray absorbent material may diffuse into micropores present in the substrate made of the X-ray transparent material. In this case, adverse effects may occur while the defect rate of products rather rises. That is, during the above-described vacuuming process, it is very important to properly adjust the degree of vacuum inside the storage tank. In the present embodiment, the vacuum pressure inside the storage tank is adjusted in the range of $1.0 \times 10^{-3}$ torr to 1 torr.

When the plurality of criss-cross type grooves formed in the substrate made of the X-ray transparent material are filled with the X-ray absorbent material through the above-described process, the X-ray absorbent material filling the criss-cross type grooves of the substrate is cured in step S250. At this time, when the substrate filled with the X-ray absorbent material is suddenly raised from the storage tank into the air at room temperature, the phase of the X-ray absorbent material filling the substrate may be rapidly changed due to a large temperature difference between the room temperature and the internal temperature of the storage tank. In this case, the substrate filled with the X-ray absorbent material may be deformed.

Thus, when the plurality of criss-cross type grooves formed in the substrate made of the X-ray transparent material are completely filled with the X-ray absorbent material, a vacuum valve is opened to remove the vacuum state inside the storage tank, while the substrate filled with the X-ray absorbent material is left in the storage tank. Then, the heater is powered off, and then the liquid X-ray absorbent material stored in the storage tank is removed to perform a pre-curing process of slowly cooling the substrate by slowly lowering the internal temperature of the storage tank.

Then, when the internal temperature of the storage tank is sufficiently lowered to a temperature of 120° C. to 150° C., the substrate filled with the X-ray absorbent material is taken out of the storage tank through the jig, and cooled at room temperature so as to cure the X-ray absorbent material filling the plurality of criss-cross type grooves formed in the transparent substrate.

Then, a grid body is formed by removing impurities remaining on the surface of the substrate through a process of milling the surface of the substrate in step S260, and a test through X-ray shooting is performed to check the quality of the grid body in step S270.

When the test of the grid is ended, a cover is attached to the front surface or either surface of the grid in step S280, in order to prevent damage to the grid. In this way, the X-ray grid is completed.

The above-described embodiment discloses the method for manufacturing the criss-cross type grid which is constituted by the substrate made of X-ray transparent material and having the criss-cross type grooves formed therein and forming a checker board shape as a whole and the X-ray absorbent material stored and cured in the criss-cross type grooves formed in the substrate, through the process of curing the X-ray absorbent material filling the criss-cross type grooves formed in the transparent substrate in step S250, and forming the grid body by removing impurities remaining on the surface of the substrate through the process of milling the surface of the substrate in step S260. In the present disclosure, however, the X-ray transparent material forming the substrate may be removed through an etching process, in order to manufacture the criss-cross type X-ray grid made of only the X-ray absorbent material having a checker board-shaped criss-cross type structure as a whole.

That is, in the above-described embodiment, the criss-cross type X-ray grid made of only the X-ray absorbent material having a criss-cross type structure having a checker board shape as a whole may be manufactured through the process of removing the X-ray transparent material forming the substrate through an etching process on the grid body, such as a wet etching process using a chemical method or a dry etching process using plasma or gas, after the grid body is formed by removing the impurities remaining on the surface of the substrate through the process of milling the surface of the substrate in step S260. Then, as in the above-described embodiment, the quality test in step S270 and the cover attaching process in step S280 may be performed to form a so-called air interspacer-type criss-cross type X-ray grid in which grid lines made of an X-ray absorbent material and having a criss-cross type structure having a checker board shape as a whole are formed, and the space between the grid lines made of the X-ray absorbent material is filled with air.

The air interspacer-type criss-cross type X-ray grid, which has the empty space formed between the grid lines made of the X-ray absorbent material and filled with the air, may raise the transmission rate of non-scattering X-ray passing through the grid, compared to the criss-cross type X-ray grid formed on the transparent substrate made of the X-ray transparent material. Thus, the air interspacer-type criss-cross type X-ray grid may further improve the quality of an X-ray image of an object.

In accordance with the embodiment of the present disclosure, the plurality of criss-cross type grooves forming a checker board shape as a whole may be formed in the horizontal and vertical directions in the substrate made of the X-ray transparent material through the sawing machine, the substrate having the criss-cross type grooves formed therein may be put into the storage tank filled with the liquid X-ray absorbent material, and the criss-cross type grooves formed in the substrate made of the X-ray transparent material may be tightly filled with the liquid X-ray absorbent material through the process of vacuuming the inside of the storage tank. Therefore, the X-ray grid manufacturing process can be further simplified, and a criss-cross type ultra-density X-ray grid which is difficult to implement through the existing stacking method can be easily manufactured.

Furthermore, since the grooves filled with the X-ray absorbent material is formed in a checker board shape on the front surface of the substrate, the scattering of the radiation can be effectively blocked in all directions (i.e. the top, bottom, left and right)

The scattered radiation blocking effect of the criss-cross type X-ray grid manufactured through the method in accordance with the present disclosure can be more clarified through comparison in radiation transmission rate between the criss-cross type grid (2D grid) formed in accordance with the embodiment of the present disclosure and a conventional straight-line grid (1D grid) constituted by only a strip in one direction.

In the criss-cross type grid applied to the present embodiment, carbon graphite was used as the transparent material, and lead was used as the absorbent material. The grooves filled with the X-ray absorbent material were manufactured in such a shape that 130 lines were formed per inch, and formed to have an aspect ratio of 8:1. The distance between the grid and the X-ray source was set to 130 cm, and the radiation transmission rate of the criss-cross type X-ray grid manufactured through the method in accordance with the present disclosure was compared to that of the 1D grid formed under the same strip condition.

For the comparison process between the radiation transmission rates, a primary radiation transmission rate Tp, a total radiation transmission rate Tt and a scattering radiation transmission rate Ts were used according to the IEC60627 standard, i.e. a performance indicator for evaluating the performance of the X-ray grid. The comparison result shows that the primary radiation transmission rate Tp and the total radiation transmission rate Tt have a relatively small difference of about 5%, but the scattering radiation transmission rate Ts of the criss-cross type grid in accordance with the present embodiment is lower by about 30 to 50% than the conventional 1D grid.

Compared to the conventional 1D grid having a scattering blocking effect only in one direction, the criss-cross type grid in accordance with the present embodiment may effectively block the scattering of the radiation in all directions (i.e. the top, bottom, left and right), thereby effectively improving the quality of an X-ray image of an object, which is taken even at the same emission amount The present disclosure described above is not limited by the above-described embodiments and the accompanying drawings, but it is obvious to those skilled in the art that the present disclosure can include various substitutions, modifications and changes without departing the technical spirit of the present disclosure.

INDUSTRIAL APPLICABILITY

The present disclosure may suggest a method which can more simplify the manufacturing process of the X-ray grid and easily manufacture a criss-cross type ultra-density X-ray grid which is difficult to implement through an existing stacking method, thereby raising the industrial applicability of the criss-cross type X-ray grid capable of effectively improving the quality of an X-ray image.

The invention claimed is:

1. A method for manufacturing a criss-cross type X-ray grid, comprising:
    forming a plurality of criss-cross type grooves at predetermined intervals in a longitudinal direction and a lateral direction in a substrate made of an X-ray transparent material, through a semiconductor sawing machine, such that the grooves form a checker board shape as a whole;
    putting the substrate having the criss-cross type grooves formed therein into a storage tank filled with a molten X-ray absorbent material;
    filling the criss-cross type grooves, formed in the substrate, with the X-ray absorbent material by vacuuming an inside of the storage tank; and
    taking the substrate filled with the X-ray absorbent material out of the storage tank, and curing the substrate at room temperature; and
    further comprising heating the storage tank filled with the molten X-ray absorbent material in the temperature range of 200° C. to 400° C.

2. The method of claim 1, wherein the criss-cross type grooves formed in the substrate are inclined at a predetermined angle toward a center from the center to a left end and a right end of the substrate.

3. The method of claim 1, wherein the substrate is made of any one selected from the group consisting of plastic, polymer, aluminum, ceramic, graphite and carbon fiber.

4. The method of claim 1, wherein the X-ray absorbent material is lead (Pb), bismuth (Bi) or an alloy of Pb and Bi.

5. The method of claim 1, wherein during the vacuuming of the inside of the storage tank, a vacuum pressure of $1.0 \times 10^{-3}$ torr to 1 torr is applied.

6. The method of claim 1, further comprising a pre-curing step of removing a heating state of the storage tank, discharging all of the X-ray absorbent material stored in the storage tank, and slowly cooling the substrate before the taking of the substrate filled with the X-ray absorbent material out of the storage tank.

7. The method of claim 1, further comprising forming a grid body by removing impurities remaining on the front surface of the substrate by milling the surface of the substrate after the taking of the substrate filled with the X-ray absorbent material out of the storage tank.

8. The method of claim 6, wherein the pre-curing step is performed until an internal temperature of the storage tank reaches a temperature of 120° C. to 150° C.

9. The method of claim 7, further comprising attaching a cover to the front surface of the grid body, after the forming of the grid body.

10. The method of claim 7, further comprising forming a criss-cross type X-ray grid made of only the X-ray absorbent material and having a criss-cross type structure with a checker board shape as a whole by removing the substrate made of the X-ray transparent substrate through an etching process, after the forming of the grid body.

11. The method of claim 10, wherein the etching process is performed through a wet etching process using a chemical method or a dry etching process using plasma or gas.

12. The method of claim 10, further comprising attaching a cover to the front surface of the criss-cross type X-ray grid after the forming of the criss-cross type X-ray grid made of only the X-ray absorbent material and having the criss-cross type structure with a checker board shape as a whole.

* * * * *